United States Patent [19]

Eastman et al.

[11] 4,310,717

[45] Jan. 12, 1982

[54] OXIDATIVE DEHYDROGENATION AND CATALYST

[75] Inventors: Alan D. Eastman; John H. Kolts, both of Bartlesville, Okla.

[73] Assignee: Phillips Petroleum Company, Bartlesville, Okla.

[21] Appl. No.: 149,601

[22] Filed: May 13, 1980

[51] Int. Cl.$^3$ ............................................. C07C 5/333
[52] U.S. Cl. .................................................. 585/661
[58] Field of Search ....................................... 585/661

[56] References Cited

U.S. PATENT DOCUMENTS

| | | | |
|---|---|---|---|
| 2,184,235 | 12/1939 | Groll et al. | 585/661 |
| 2,648,639 | 8/1953 | Bennett | 585/661 |
| 2,687,987 | 8/1954 | Bennett | 585/661 |
| 2,824,843 | 2/1958 | Dietzler et al. | 585/661 |
| 3,810,953 | 5/1974 | Cichowski | 252/437 |
| 3,926,845 | 12/1975 | Cichowski | 252/432 |
| 4,000,058 | 12/1976 | Duhaut et al. | 208/138 |
| 4,243,826 | 1/1981 | Antos | 585/434 |

*Primary Examiner*—Delbert E. Gantz
*Assistant Examiner*—O. Chaudhuri

[57] ABSTRACT

Hydrocarbons are oxidatively dehydrogenated in the presence of a catalyst comprising a mixture of oxides of manganese, phosphorus, and an alkali metal, optionally, supported on a refractory oxide. In one embodiment, ethane is converted to ethylene in the presence of a catalyst comprising a mixture of oxides of manganese, phosphorus, and sodium supported on alumina.

7 Claims, No Drawings

OXIDATIVE DEHYDROGENATION AND CATALYST

The present invention relates to catalytic compositions and to chemical conversion processes using the catalysts. In accordance with another aspect, this invention relates to a process for the oxidative dehydrogenation of hydrocarbons in the presence of a catalyst comprising manganese, phosphorus, and an alkali metal with, or without, a refractory support. In accordance with a further aspect, this invention relates to the oxidative dehydrogenation of paraffinic hydrocarbons to the corresponding mono-olefins in the presence of a catalyst comprising a mixture of oxides of manganese, phosphorus, and an alkali metal. In accordance with a further aspect, this invention relates to a catalytic composition comprising a mixture of oxides of manganese, phosphorus, and an alkali metal with, or without, a refractory support.

BACKGROUND OF THE INVENTION

It is a continuing goal of the chemical processing industries to find both primary and alternative methods for converting raw materials, which are readily available, into other materials which may be less plentiful and more valuable. Some of the more useful of such conversion methods is dehydrogenation processes for the conversion of organic compounds, such as hydrocarbon feedstocks to unsaturated compounds. A number of catalytic processes have been developed which have attained some measure of commercial success. There is a continuing search to develop catalytic materials and processes which are more efficient in minimizing side reactions, improving conversion rates, improving yields and selectivities to desired end porduct, or which have a low susceptibility to deactivation, e.g., are capable of extended periods of operation without regeneration and/or which can be readily regenerated to an activity approaching that of fresh catalysts. The present invention relates to a novel catalyst composition which is useful in the oxidative dehydrogenation of hydrocarbons.

Accordingly, an object of this invention is to provide an improved process for the oxidative dehydrogenation of hydrocarbons.

Another object of this invention is to provide a novel catalyst composition.

A further object of this invention is to provide a catalytic composition useful in the oxidative dehydrogenation of hydrocarbons.

Other aspects, objects, and the several advantages of this invention will become apparent to those skilled in the art upon reading this disclosure and the appended claims.

The present invention provides a novel catalyst and a novel process for the conversion of hydrocarbon feedstocks to hydrocarbons having a greater degree of unsaturated and which have the same and sometimes lower number of carbon atoms as in the hydrocarbon feed.

In accordance with the invention, hydrocarbons and, particularly, paraffinic hydrocarbons are oxidatively dehydrogenated to unsaturated product or products having a greater degree of unsaturation by contacting such hydrocarbons under dehydrogenation conditions in the presence of a catalyst mixture comprising manganese, phosphorus, and an alkali metal with, or without, a refractory support.

In accordance with one embodiment of the invention, light paraffinic hydrocarbons are oxidatively dehydrogenated to the corresponding mono-olefins by contacting same under oxidative dehydrogenation conditions in the presence of a catalyst mixture of oxides of manganese, phosphorus, and alkali metal with, or without, a refractory support.

In accordance with the invention, paraffinic hydrocarbons can be converted in good yields to mono-olefins. The invention is particularly suitable for the conversion of ethane to ethylene, butane to butene, isopentane to isoamylene, and the like.

Further, in accordance with the invention, a novel catalyst is provided comprising a mixture of oxides of manganese, phosphorus, and an alkali metal with, or without, a refractory support.

CATALYST

The catalyst of this invention comprises manganese oxide, phosphorus oxide, and at least one element from Group Ia of the Periodic Table, also as the oxide. The members of this group are lithium, sodium, potassium, rubidium, and cesium. The atomic ratio in which manganese:phosphorus:alkali metal elements are combined to form the catalyst is 1:0.03 to 0.25:0.06 to 0.30, respectively. Preferably the ratio, expressed in the same manner and in the same order, is 1:0.05 to 0.20:0.10 to 0.30.

Although it is not necessary, it is preferable for the catalyst to be prepared on a refractory oxide that is suitable for a support, e.g., activated alumina, magnesia, zinc aluminate, and the like. The atomic ratio of manganese to metal atoms in the support can range from about 0.6 to about 1.5, preferably the ratio is about unity.

A suitable method for preparing the supported catalyst is to impregnate the support (of suitable particle size) alternately with solutions of manganese and of alkali metal phosphate by the method of incipient wetness. After each impregnation, the preparation is dried in an oven to remove the solvent. After addition of the catalyst to the support has been completed, the catalyst is prepared for use by calcining in air at about 800° C. for three hours.

Unsupported catalyst is conveniently prepared by mulling a suitable manganese compound with a solution that contains both phosphorus and the alkali metal until a smooth, uniform slurry-like product has been obtained. This is dried in an oven to remove water, then calcined in air at about 800° C. for three hours.

For preparation by impregnating a porous, refractory oxide manganous nitrate, $Mn(NO_3)_2$, is preferred. Unsupported catalysts ca be made from manganous acetate, manganese carbonate $MnCO_3$, or manganese dioxide $MnO_2$. Phosphorus and the alkali metal M can be incorporated from solutions of orthophosphoric acid and the alkali compounds $MOH$, $M_2CO_3$, $MHCO_3$, and the like. Or, for convenience, compounds which contain both elements such as the orthophosphates $MH_2PO_4$, $M_2HPO_4$, and $M_3PO_4$, and the pyrophosphate $M_4P_2O_7$ can be used.

OXD PROCESS

Oxidative dehydrogenation (OXD) of paraffins to olefins using the catalyst of this invention is believed to involve the reaction of two hydrogen atoms from the paraffin with an atom of oxygen from the catalyst to produce, in addition to an olefin molecule, a molecule of water. The process is effected in a cyclic manner in which the catalyst is contacted alternately with a paraffinic hydrocarbon, then with a free oxygen-containing gas such as air.

Paraffins amenable to dehydrogenation range from ethane to dodecane although it is preferable to use the lighter paraffins ranging from ethane to pentane. These can be branched or unbranched. The use of this catalyst to convert ethane to ethylene is particularly preferred. Some specific examples of other feeds include propane, butane, isobutane, pentane, octane, dodecane, 2-methylhexane, 2,4-dimethyloctane, and the like, including mixtures thereof. Heavier feedstock can be treated at the same pressures and residence times that are suitable for ethane, but the temperature for their treatment generally decreases with increasing carbon number within the temperature range described below.

The dehydrogenatable feedstocks can be converted, according to the process of the present invention, under any suitable conditions so long as conditions are such to oxidatively dehydrogenate the hydrocarbon or hydrocarbons to mono-olefins. Thus, the conditions of temperature, pressure, and period of contact will vary depending upon the particular feedstock and catalyst combination but, in any event, the conditions are sufficient to dehydrogenate the paraffinic hydrocarbon to the corresponding mono-olefin.

The temperature for oxidative dehydrogenation can range between about 600°–800° C. For ethane, the preferred temperature ranges between about 675°–740° C. Catalyst activity is retained longer by starting to use a previously unused catalyst at temperatures lower than these, e.g., about 550° C., then increasing to the range stated here during the first few process cycles.

Below pressures at which the olefin product begins to polymerize OXD conversion is not greatly affected by reaction pressure. Suitable pressure for operation is in the range of 10 to 520 kPa; preferably the reaction is run at about 100–200 kPa.

Reactant feed rate, expressed as volumes of gas at standard conditions per volume of catalyst per hour (GHSV) can range between 200–1000; a rate between about 400–600 is preferred.

Of considerable importance to the OXD process is the length of the process cycle in which paraffins are contacted with the catalyst before the catalyst is regenerated. At the conclusion of the regeneration cycle, the manganese in the catalyst is believed to be present as $Mn_3O_4$. The quantity of paraffins that is contacted with catalyst before the next regeneration period preferably will not exceed that which will convert all $Mn_3O_4$ to MnO, i.e., the number of moles of hydrocarbon fed in one process cycle will not exceed the number of moles of $Mn_3O_4$ in the catalyst zone. Although MnO is not readily reduced further it will be ineffective to dehydrogenate additional feed and, in addition, becomes more difficultly regenerable.

Although it is not required, prudent operation may dictate a purge of the reactor with an inert gas, e.g., nitrogen or carbon dioxide, between dehydrogenation and regeneration cycles to avoid mixing hydrocarbons with free oxygen.

Preparation of some catalysts and results of their use to convert ethane to ethylene as shown in the following examples.

EXAMPLE I

Catalyst A was a supported catalyst prepared by impregnating activated alumina. 100 g of Filtrol 86 alumina was impregnated with 484 g (1.35 moles) of 50% $Mn(NO_3)_2$ using sixteen 30 g portions. After each addition, the catalyst was dried at 150° C. for 6–10 hours before the next step. A total of 19 g (0.043 moles) of $Na_4P_2O_7.10H_2O$ dissolved in 60 mL of water was added—half when one half of the manganese had been added and the other half when only one portion of manganese nitrate remained to be added. After impregnation had been completed, catalyst A was dried at 150° C. for 24 hours, then calcined in air at 704° C. for three hours. The atomic ratio Mn:P:Na in catalyst A was calculated to be 1:0.10:0.20.

Catalyst B was prepared from catalyst A by adding one gram of $Na_4P_2O_7.10H_2O$ to 30 g of the latter by impregnation with aqueous solution; then drying and calcining in air as for catalyst A. The atomic ratio Mn:P:Na in catalyst B was calculated to be 1:0.14:0.28.

Catalysts C, D, E, and F were prepared from different manganese compounds and contained no catalyst support. All had the same atomic ratio Mn:P:Na=1:0.067:0.133. They were made as follows. Catalyst C was prepared by adding excess ammonium hydroxide to 107 g manganous nitrate dissolved in about one liter of water. After heating to remove most of the ammonia, it was filtered, and 8.94 g $Na_4P_2O_7.10H_2O$ dissolved in a minimum volume of water was mixed thoroughly with the filter cake. Catalyst D was prepared by mixing 69.0 g of powdered manganese carbonate with 60 mL of solution containing 8.92 g of $Na_4P_2O_7.10H_2O$. Catalyst E was prepared by dissolving 147 g of $Mn(C_2H_3O_2)_2.4H_2O$ and 8.92 g $Na_4P_2O_7.10H_2O$ in about 600 mL of water and heating on a hot plate until the volume of solution was reduced to about 100 mL. Catalyst F was prepared by mixing 52 g of manganese dioxide powder with about 60 mL of solution containing 8.9 g of $Na_4P_2O_7.10H_2O$. Ten grams of powdered starch was then added to the mixture. Preparation of catalysts C through F was completed by drying the mixtures described in an oven at about 120° C., then calcining them in air at 820° C. for three hours.

EXAMPLE II

Supported catalysts A and B were used in runs to produce ethylene from ethane by OXD. Fifteen mL portions of $-16+40$ mesh catalyst were placed in a quartz reactor in a temperature controlled furnace and contacted alternately with ethane at 400 GHSV for three minutes, then with an equal volume mixture of air plus nitrogen, each flowing at 1200 GHSV, for six minutes. The runs contined for 900 cycles, and results of analyses on samples taken during that period are presented in Table I. Analyses were made on snap samples taken 1.5 minutes into the process period.

TABLE I

| Cycle | Temp. °C. | A Conv.,% | A Selectivity,% | B Conv.,% | B Selectivity,% |
|---|---|---|---|---|---|
| 1 | 650 | 39 | 54 | 27 | 63 |
| 2 | 650 | 41 | 62 | 45 | 65 |
| 3 | 700 | 43 | 70 | 54 | 75 |
| 10 | 700 | 45 | 70 | 55 | 80 |
| 425 | 700 | 37 | 84 | 52 | 78 |
| 650 | 700 | 23 | 86 | — | — |
| 765 | 700 | — | — | 16 | 90 |

TABLE I-continued

| Cycle | Temp. °C. | A Conv.,% | A Selectivity,% | B Conv.,% | B Selectivity,% |
|---|---|---|---|---|---|
| 900 | 700 | 22 | 93 | 16 | 96 |

During the first few cycles the activity and selectivity of both catalysts increased. Then, as the catalysts aged further, activity tended to decline while the selectivity to ethylene continued to increase.

Unsupported catalysts C through F were used in runs made in a somewhat different manner. Two mL portions of −16+40 mesh catalyst in quartz reactors in a temperature controlled furnace were contacted as follows. Nitrogen flowed continuously at 500 GHSV. During the four minute regeneration cycle air at 2500 GHSV was combined with the nitrogen. Flow of air was discontinued for two minutes to provide a nitrogen purge, ethane was then combined with nitrogen, also at 500 GHSV, for a 2.5 minute OXD period. Flow of ethane was discontinued for two minutes to provide another nitrogen purge, then regeneration was repeated. Three snap samples from the OXD portion of each cycle were collected and analyzed. Table II records the results of the average of these three analyses for catalysts C-F, and also using corundum only. All runs were made at 703° C.

TABLE II

| Catalyst | Cycle | $C_2H_6$ conv., % | Sel. to $C_2H_4$, % |
|---|---|---|---|
| C | 1 | 97.2 | 50.9 |
|   | 5 | 97.4 | 70.3 |
|   | 127 | 38.3 | 69.8 |
| D | 1 | 75.0 | 75.7 |
|   | 5 | 57.4 | 85.1 |
|   | 127 | 14.4 | 93.6 |
| E | 1 | 35.7 | 86.3 |
|   | 5 | 33.5 | 88.0 |
|   | 127 | 7.5 | 93.9 |
| F | 1 | 31.9 | 87.9 |
|   | 5 | 22.5 | 89.3 |
|   | 127 | 5.9 | 91.2 |
| Corundum | 1 | 19.8 | 90.1 |
|   | 5 | 18.0 | 92.1 |
|   | 127 | 14.7 | 93.0 |

These unsupported catalysts are also active and selective, particularly during the first process cycles, to convert ethane to ethylene by oxidative dehydrogenation.

We claim:

1. An oxidative dehydrogenation process which comprises contacting at least one paraffinic hydrocarbon with a catalyst consisting essentially of a mixture of oxides of manganese, phosphorus, and an alkali metal wherein the atomic ratio of manganese:phosphorus:alkali metal is 1:0.03 to 0.25:0.06 to 0.30 under oxidative dehydrogenation conditions sufficient to convert said paraffinic hydrocarbon to the corresponding mono-olefin.

2. A process according to claim 1 wherein said paraffinic hydrocarbon is ethane.

3. A process according to claim 1 wherein said catalyst is combined with a refractory oxide support and the atomic ratio of manganese to metal atoms in the support ranges from about 0.6 to about 1.5.

4. A process according to claim 1 wherein said alkali metal is sodium.

5. A process according to claim 1 which is carried out in a cyclic manner in which the catalyst is contacted alternately with a paraffinic hydrocarbon and then with a free oxygen containing gas.

6. A process according to claim 1 wherein said paraffinic hydrocarbon is ethane which is converted to ethylene and said catalyst is manganese, phosphorus, and sodium.

7. An oxidative dehydrogenation process which comprises contacting ethane with a catalyst consisting essentially of a mixture of oxides of manganese, phosphorus and an alkali metal combined with activated alumina as a support, wherein the atomic ratio of manganese:phosphorus:alkali metal is 1:0.03 to 0.25:0.06 to 0.30, under oxidative dehydrogenation conditions sufficient to convert said ethane to ethylene.

* * * * *